(12) United States Patent
Kirkland

(10) Patent No.: US 6,420,436 B1
(45) Date of Patent: *Jul. 16, 2002

(54) IMAGING CONTRAST MEDIA AND METHODS OF USE

(75) Inventor: W. Dean Kirkland, El Cajon, CA (US)

(73) Assignee: Alliance Pharmaceutical Corp., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/100,053

(22) Filed: Jun. 19, 1998

Related U.S. Application Data

(63) Continuation of application No. 08/481,057, filed on Jun. 7, 1995, now Pat. No. 5,770,181, which is a continuation of application No. 07/685,211, filed on Apr. 12, 1991, now Pat. No. 5,496,535.

(51) Int. Cl.$^7$ .............................................. A61K 47/00
(52) U.S. Cl. .................. 514/772; 514/743; 514/746; 514/925; 514/927; 514/964; 424/9.37; 424/9.4
(58) Field of Search ................................ 514/772, 743, 514/746, 925, 927, 964; 424/9.37, 9.4

(56) References Cited

U.S. PATENT DOCUMENTS

| | | | |
|---|---|---|---|
| 3,592,185 A | * | 7/1971 | Frei et al. |
| 3,975,512 A | | 8/1976 | Long |
| 4,074,709 A | | 2/1978 | Kaplan |
| 4,120,946 A | | 10/1978 | Queille et al. |
| 4,215,103 A | | 7/1980 | Millington |
| 4,927,624 A | | 5/1990 | Bryant et al. |
| 4,951,673 A | * | 8/1990 | Long ........................ 129/653 |
| 4,971,785 A | | 11/1990 | Wilson et al. |
| 4,994,258 A | | 2/1991 | Burns et al. |
| 5,788,665 A | | 8/1998 | Sekins et al. |

FOREIGN PATENT DOCUMENTS

| | | |
|---|---|---|
| DE | 2804234 | 8/1978 |
| EP | 0118281 | 9/1984 |
| EP | 0401377 | 12/1990 |
| EP | 9103267 | 3/1991 |
| WO | 9001901 | 3/1990 |
| WO | 9014846 | 12/1990 |

OTHER PUBLICATIONS

File Server Derwent, File WPI, Abstract No. 76–58263X, & JP, A, 50027399 (Miyata Ind KK) Mar. 20, 1975, see abstract.

File Server Derwent, File WPI, Abstract No. 71–01668s, & US, A, 3553127 (ANSUL CO.) Jan. 5, 1971, see abstract.

SMRI Brochure from 9$^{th}$ annual meeting, Apr. 13–17, 1991.

CAS Online Printout of Medline 89308841, Sato et al, May 1989.*

* cited by examiner

Primary Examiner—Samuel Barts
(74) Attorney, Agent, or Firm—Knobbe Martens Olson & Bear LLP

(57) ABSTRACT

This invention relates to a non-aqueous fluorocarbon composition for use in magnetic resonance imaging (MRI) or radiographic imaging (X-ray or computed tomography), particularly imaging of the gastrointestinal (GI) tract; an improved fluorocarbon composition with enhanced contrast effects in the GI tract; a fluorocarbon composition having improved palatability; a fluorocarbon composition for delivering drugs or bioactive agents; improved preparations for radiographic imaging or MRI; methods for producing and using such preparations; methods for improving the palatability of non-aqueous liquids; and methods for improving imaging.

7 Claims, No Drawings

IMAGING CONTRAST MEDIA AND METHODS OF USE

CROSS REFERENCE TO RELATED APPLICATION

This is a continuation of U.S. Ser. No. 08/481,057, filed Jun. 7, 1995, now U.S. Pat. No. 5,770,181, issuing Jun. 23, 1998, which is a continuation of U.S. Ser. No. 07/685,211, filed Apr. 12, 1991, now U.S. Pat. No. 5,496,535, issued Mar. 5, 1996.

FIELD OF THE INVENTION

The present invention relates to radiological imaging systems, and more particularly to use of a contrast enhancing agent in magnetic resonance imaging (MRI), computed tomography (CT), or conventional radiography (X-ray). In particular, this invention relates to improved fluorocarbon-based contrast agents with enhanced contrast effects in the gastrointestinal (GI) tract, which agents may require a lesser amount of fluorocarbon to be effective, thereby reducing costs and increasing patient compliance. This invention also relates to an improved fluorocarbon composition having improved palatability, and to fluorocarbon compositions for delivering active agents, including pharmacological and bioactive agents. The invention further relates to methods for producing such preparations.

BACKGROUND OF THE INVENTION

Contrast agents are useful adjuncts in radiological imaging because they make it possible to determine the location, size and conformation of organs or other structures of the body in the context of their surrounding tissues. Cells which make up the tissues of soft non-bony body parts are comprised primarily of water, even among parts that differ markedly in shape and structure such as the liver, pancreas and intestine. Radiography procedures of CT and MRI operate on the basis of distinct physical principles, and each detects and maps variances in the composition of a target object. These imaging techniques can therefore be used to differentiate between normal tissue and tumors, lesions, or blockages. Small tumors and overlapping tissues, however, are difficult to distinguish. In the diagnosis of disorders of the GI tract, for example, blockage or abnormalities in the conformation of loops of intestine lying one on the other are difficult to identify unless the section of the GI tract is filled with a contrast agent which enables definition of volumes and delineation of boundaries.

In the conventional radiographic procedure, a beam of X-rays passes through a target object and exposes an underlying photographic film. The developed film then provides an image of the radiodensity pattern of the object. Less radiodense areas produce a greater blackening of the film; more radiodense, bony tissues produce a lighter image. Effective contrast agents for X-ray may be either less radiodense than body tissues or more radiodense. The less radiodense agents include air and other gases; an example of a more radiodense contrast material is a barium sulfate suspension.

Computed tomography (CT) is superior to conventional radiography in its ability to image, with extremely high resolution, a succession of thin sections of an object at specific points, lines or planes along the X, Y, or Z axis of the target object. However, because this procedure is also based on the detection of differences in radiodensity, requirements for contrast agents in CT are essentially identical with those for conventional radiography.

Magnetic resonance imaging (MRI) systems for body imaging operate on a different physical principle. Literature describing the theoretical and practical use of MRI systems is available from manufacturers such as General Electric & Co., which markets commercial systems. In general, advantage is taken of the fact that some atomic nuclei, e.g., hydrogen nuclei, have both nuclear spin and nuclear magnetic moment, and therefore can be manipulated by applied magnetic fields. In the conventional type of MRI system, a magnetic field is established across a body to align the spin axes of the nuclei of a particular chemical element, usually hydrogen, with the direction of the magnetic field. The aligned, spinning nuclei execute precessional motions around the aligning direction of the magnetic field. For the aligned, spinning nuclei, the frequency at which they precess around the direction of the magnetic field is a function of the particular nucleus which is involved and the magnetic field strength. The selectivity of this precessional frequency with respect to the strength of the applied magnetic field is very sharp, and this precessional frequency is considered a resonant frequency.

In a customary MRI system, after alignment or polarization of the selected nuclei, a burst of radio frequency energy at the resonant frequency is radiated at the target body to produce a coherent deflection of the spin alignment of the selected nuclei. When the deflecting radio energy is terminated, the deflected or disturbed spin axes are reoriented or realigned, and in this process radiate a characteristic radio frequency signal which can be detected by an external coil and then discriminated in the MRI system to establish image contrast between different types of tissues in the body. MRI systems have a variety of different excitation and discrimination modes available, which are known in the art.

Contrast agents for MRI must possess a substantially different concentration of the nuclei used as a basis for scanning. In a hydrogen scanning system, an agent substantially lacking hydrogen can be used; in an MRI system which scans for a physiologically minor nucleus, e.g., fluorine nuclei, a substance with a high concentration of that nucleus would provide appropriate contrast.

Contrast agents may be introduced into the body space in various ways, depending on the imaging requirement. In this application, emphasis is placed on oral administration, albeit other modes may also be appropriate. A suitable contrast agent must be biocompatible, that is, non-toxic and chemically stable, not absorbed by the body or reactive within the tissue, and eliminated from the body within a short time. Efforts to enhance imaging have also included the use of $CO_2$ gas, which is known to have an enhancing effect, particularly in the GI tract. Few satisfactory agents have been developed for MRI, although many have been tried. For example, GI imaging has been enhanced with mineral oil.

It is known to use fluorocarbons, including brominated perfluorocarbons, as a contrast enhancement medium in radiological imaging as shown in U.S. Pat. No. 3,975,512 to Long. Brominated and other fluorocarbons are known to be safe and biocompatible when used in the body. It is also known to use these agents in the context of the MRI procedure to contrast more clearly and more distinctly in MRI-produced images the several body parts which normally have substantially higher water content and which are close or overlaid one on the other, as in the GI tract.

Previous investigations into the effectiveness of radiological examination of the GI tract have revealed that conventional contrast media, such as barium or clay-based media taken by the patient prior to such examination, do not enable small lesions, such as shallow ulcers, and flat or surface ulcers, to be accurately detected. Moreover, few contrast media are as ideally suited for use in MRI as well as in diagnostic radiological applications, as are the fluorocarbons.

An early proposal suggested that air be directly introduced into the desired location in the intestine by means of a tube (see, e.g., U.S. Pat. No. 4,074,709). Subsequently, in conjunction with the use of barium and clay-based contrast media, it was proposed that one might expand or distend the part under examination by directly introducing powder, granules or tablets into the medium which would then release carbon dioxide into the intestine; this, too, did not prove entirely effective. Maintaining the gas in aqueous medium also proved to be a problem and often required the use of a pressurized vessel to dissolve the gas in the contrast solution (see, e.g., U.S. Pat. No. 4,215,103).

None of these techniques was entirely satisfactory; moreover, they could cause the patient great discomfort, especially if distension of the GI tract was not strictly controlled. Moreover, even if these proposals had proven effective for use with the aqueous contrast media with which they were tested, such methods are not transferable to fluorocarbon contrast media, which lack water content as found in the barium and clay-based media.

Another problem common to contrast media is their general unpalatability. Fluorocarbon media, like barium and clay contrast solutions, do not tend to be extremely palatable; in fact, patients often describe fluorocarbon liquids as having a "slick" mouth-feel. In addition, the taste of the contrast media is often unpleasant. Unlike aqueous media, however, fluorocarbon contrast agents, principally due to their hydrophobic nature, do not accept liquid flavoring agents that have been used more-or-less successfully with barium or clay-based solutions.

Accordingly, the present invention is addressed to the improvement of fluorocarbon compositions, especially for use in imaging the GI tract. In addition, more palatable fluorocarbon compositions are disclosed herein.

SUMMARY OF THE INVENTION

Therefore, in accordance with one object of the present invention, improved MRI and radiographic imaging via the use of $CO_2$-generating means suspended in a biocompatible fluorocarbon composition or contrast medium is provided. Another object of the present invention is to provide a fluorocarbon composition or contrast agent for use with MRI or radiographic imaging, wherein the composition has enhanced palatability to the patient.

In one embodiment of the invention, a biocompatible composition comprising a fluorocarbon liquid in admixture with an effective amount of a particulate, fluorocarbon-insoluble, gas-generating, palatability-enhancing, pharmacological, or bioactive agent is disclosed. In another variation, the medium is any non-aqueous material. In various embodiments, the gas-generating agent comprises, for example, sodium bicarbonate, sodium carbonate, calcium carbonate, potassium bicarbonate, or mixtures thereof. Another variation suggests combining the gas-generating agent with a non-toxic release-controlling material. In yet another variation, the agent further comprises dry acid powder; in alternate embodiments, the acid powder comprises, for example, one or more of citric acid, adipic acid, malic acid, ascorbic acid, tartaric acid, or fumaric acid. In other embodiments, the gas generated comprises carbon dioxide, other gases, or a mixture thereof.

Alternative modes include a composition further comprising a palatability-enhancing agent. The palatability-enhancing agent may comprise a flavoring agent, or it may comprise a flavorless substance. In one embodiment, the palatability-enhancing agent is powdered or granular. In another embodiment, it may further comprise filler ingredients, such as starch, dextrins, and other carbohydrates. In a simple form, the composition may comprise a fluorocarbon and bicarbonate.

The compositions of the present invention may be used with radiological imaging systems including MRI, CT, or X-ray. In various embodiments, the present invention discloses methods of imaging using the compositions disclosed herein.

The present invention also suggests methods of making the disclosed contrast media. In one embodiment, the method comprises suspending in the medium an effective amount of a gas-generating or palatability-enhancing agent, or both. In one embodiment, the gas-generating agent is a bicarbonate. In another variation, dry acid powder is added to the medium. In yet another variation, the agent(s) is/are added extemporaneously; in another, each agent may be added at the time of manufacture.

In an alternative embodiment, the gas-generating agent is combined with a non-toxic release-controlling substance. In other embodiments, the agent added to the fluorocarbon composition is a pharmacological agent or a bioactive agent.

Yet another embodiment suggests the further step of adding filler ingredients. In various embodiments, these filler ingredients may comprise starches, sugars, mono- and disaccharides, and other carbohydrates; hydrolysates (e.g., dextrin); polymers (e.g., pectin, dextran, cellulose and cellulose derivatives); poly-hydric alcohols (e.g., sorbitol, mannitol); minerals (e.g., clays, bentonite, silica and derivatives); protein derivatives (e.g., casein, powdered milk) and the like.. In other embodiments, filler ingredients may include one or more oils.

This invention may also be used to enhance the palatability of other non-aqueous materials, such as oils. These oils include, without limitation, avocado, mineral, castor, soybean, canola, palm, palm seed, safflower, sesame, corn, sunflower, cottonseed, or olive oil. Orally-ingested oils including, without limitation, the above-mentioned varieties, are used for dietary and therapeutic purposes—for example, as laxatives. The present invention provides a means for adding flavorings to previously-unpalatable substances.

DETAILED DESCRIPTION OF THE INVENTION

As noted previously, studies have revealed that conventional aqueous contrast media, such as barium or clay-based media, taken by the patient prior to radiographic examination, do not enable small lesions, such as shallow ulcers, and flat or surface ulcers, to be accurately detected, nor do such media enable one to reliably detect any difference between benign and malignant ulcers. Moreover, very few contrast media are as ideally suited for use in MRI as well as in diagnostic radiological applications, as are the fluorocarbons.

For MRI, one looks to materials that have adequate nuclear or relaxation properties for imaging that are different from the corresponding properties of the tissue being imaged. Either an imageable nucleus (such as $^{19}F$) or a ferromagnetic or paramagnetic material can be used with appropriate MRI equipment.

For X-ray and CT imaging, the contrast agent should have an adequate electron density to render it visible with these techniques. Suitable electron density is achieved, e.g., in compounds with bromine or iodine moieties, and in materials comprising or including radiopaque metal atoms.

Preferred contrast agents include perfluorooctylbromide ("PFOB") and other radiopaque perfluorocarbons, imageable fluorocarbon compounds, perfluoroalkylated ethers and perfluoroalkylated ether bromides.

Fluorocarbons, unlike aqueous contrast media, are typically not amenable to the addition of liquids. Until the advent of the present invention, it was believed that the addition of flavoring agents would not be practical for use with fluorocarbons. However, it has now been found that virtually any powder reactive with an aqueous system can be used with fluorocarbon contrast media.

In particular, it has been found that powders, while they are not soluble with the fluorocarbon liquid, suspend well enough in the liquid to allow the powder to be transported along with the liquid. Then, when the fluorocarbon medium comes into contact with a moist surface, such as the oral or other gastrointestinal mucosa, the powdered substance interacts or reacts with the moist surface, producing the desired effect. This effect may be the sensation of flavor, or any other desired result. In addition, due to the success observed in using flavoring and other palatability-enhancing agents, delivery of a gas-producing agent has also been attempted, with successful results. These observations further support the conclusion that delivery of a medication, a palliative agent, or similar substances may also be accomplished since, as noted earlier, virtually any powder can be used with fluorocarbon or any non-aqueous medium. While this is certainly contrary to expectations, it has been found to be effective, as set out in greater detail below.

In an effort to improve non-aqueous fluorocarbon compositions, especially for use in imaging the GI tract, combinations of $CO_2$-producing effervescent powder and fluorocarbon contrast medium were tested to determine whether these might produce MRI GI contrast agents superior to fluorocarbon alone. Since fluorocarbons—e.g., perfluorooctylbromide (PFOB)—produce a signal void on MRI, and have demonstrated safety and efficacy in Phase II clinical trials, enhancement and utilization of these qualities was—and is—desirable. Since perfluorocarbon contrast media, such as PFOB, are heavier than aqueous fluids, they tend to layer with bowel contents and best enhance dependent portions of the GI tract. $CO_2$ gas, on the other hand, is lighter than aqueous bowel contents and best enhances superior portions of the GI tract. It is known that the use of safe and effective $CO_2$ gas enhances the effects of contrast agents. The addition of $CO_2$ to fluorocarbon agents would therefore decrease the amount of fluorocarbon required, which tends to produce additional benefits, such as the reduction of costs and increased patient compliance.

Dry, powdered ingredients used for generating carbon dioxide gas are suspended in a fluorocarbon, preferably a perfluorocarbon such as PFOB, or in other non-aqueous fluids. These dry ingredients may be sodium bicarbonate and/or any one of many dry acid powders, such as citric acid. These powders may be added extemporaneously or at the time of manufacturing. No reaction occurs until the dry ingredients come in contact with fluids of the mouth, stomach, or intestinal tract, at which time, carbon dioxide gas is generated. Sodium bicarbonate, which will react with stomach acid, may be incorporated alone, as it is capable of generating carbon dioxide in the stomach.

Prior to the development of the present invention, $CO_2$-generating ingredients were typically added to a container of water and were ingested while the carbon dioxide-generating reaction was occurring. Obviously, a substantial portion of carbon dioxide gas is lost into the atmosphere during this procedure, as well as during ingestion and subsequent eructation. This makes the amount of gas ingested difficult to control, and difficult, if not impossible, to quantitate.

The degree, location, and timing of carbon dioxide generation may be regulated, for example, by controlling particle size or by coating one or more of the "reactive" ingredients so that it dissolves in a specific, predetermined body fluid. The particular type of particle or time-release agent can be selected from a wide range of substances and compositions known in the art. For example, polymers of appropriate particle size, colloids, and emulsions are all within the scope of the present invention. Liposomes may also be used to transport gas-generating substances.

In a similar manner, pharmacologic or bioactive agents may be delivered to a specific site or general area via coupling the agent to release-controlling agents such as those noted above. Moreover, as methods of coupling ligands (for example, antibodies) to other molecules—including molecules as diverse as polymers, liposomes, and polypeptides—are known in the art, pharmacologic or bioactive agents may be coupled to such ligands directly, or may be encapsulated in a lipid or liposomal coating, for example. Then, these coupled agents may be mixed with the fluorocarbon prior to their administration to a patient. In this manner, the coupled agent, suspended in the fluorocarbon, may be delivered to the desired site or the entire GI system. For example, this would allow medication to be delivered directly to ulcerated sites in the GI tract and would simultaneously allow the patient to undergo a diagnostic imaging procedure.

It is also an object of the present invention to make fluorocarbons more palatable to the patient; this tends to increase patient compliance. Unlike liquid flavor ingredients, which are not soluble in fluorocarbon contrast media such as PFOB, powdered flavoring ingredients can be suspended in these non-aqueous fluorocarbon media prior to their ingestion. While suspended, the flavoring ingredients are non-reactive. When ingested, however, the suspended flavoring ingredients dissolve in the fluids of the mouth and immediately impart the desired flavor.

Preferably, the suspended ingredient particles are small enough to remain in suspension for at least about 2 minutes. Use of the term "particles" should not be construed as being limiting; it includes powders, crystals, granules, and the like. Particle sizes averaging about 5mm or less may be used; particle sizes averaging about 2mm or less are preferred. Mouth-feel is also improved by the suspension of insoluble ingredients; this feeling may be enhanced further via the addition of filler ingredients such as starch, sugars, mono- and disaccharides, and other carbohydrates; hydrolysates (e.g., dextrin); polymers (e.g., pectin, dextran, cellulose and cellulose derivatives); poly-hydric alcohols (e.g., sorbitol, mannitol); minerals (e.g., clays, bentonite, silica and derivatives); protein derivatives (e.g., casein, powdered milk) and the like.

EXAMPLE 1

A commercial packet (4 grams) of E-Z-GAS II™ was powdered and added to approximately 50 mL of PFOB, which was then administered to human clinical subjects. The packet consisted of sodium bicarbonate, citric acid, and simethicone. The suspension was non-reactive until exposed to mouth fluids and other GI fluids. At this time, $CO_2$ gas was generated.

EXAMPLE 2

A flavored sample was administered in the same manner as in Example 1. Two grams of E-Z-GAS II™ powder and ¼ teaspoon (tsp) of sugar-free Tang® were added to approximately 50 mL of PFOB and administered to human test subjects, with favorable results reported.

EXAMPLE 3

T1 weighted images of canine abdomens were obtained on a 1.5 Tesla MRI scanner before and after nasogastric administration of 10 mL/kg of either PFOB (n=3) or PFOB blended with a sodium bicarbonate/citric acid mixture (n=5). Each study was scored independently by four blinded readers according to the percentage of bowel loops with black lumens. The ratings of bowel filling increased by 338 percent in the PFOB plus $CO_2$ group (p<0.001) and by 194 percent in the PFOB group (p<0.01) compared with the pre-contrast studies. Although PFOB plus $CO_2$ was rated as a better GI contrast agent than PFOB alone, the difference in degrees of increase between these two agents did not reach the cut off level for statistical significance (p=0.06).

This study suggests that the addition of $CO_2$ gas to PFOB improves bowel enhancement and further demonstrates the suitability for use of compositions made according to the present invention with MRI methods. The proposed clinical dose of PFOB is approximately half that of the dose that we studied. When using the smaller volume of PFOB, the addition of $CO_2$ gas could greatly improve bowel enhancement, especially of the upper GI tract.

EXAMPLE 4

Approximately 0.5 grams of flavoring agent was added to approximately 50 mL of PFOB. The following flavoring agents were used:

1. Sugar-free instant coffee, Suisse Mocha flavor.
2. Equal parts of Hershey's® cocoa powder, powdered sugar, ARA® creamer, and Equal® (NutraSweet®) sweetener (aspartame).
3. Lipton® sugar-free iced tea.
4. Sugar-free Kool-Aid®, cherry flavor.
5. Sugar-free Tang®.
6. Sugar-free Crystal Light®, fruit punch flavor.
7. Unsweetened Kool-Aid®, grape flavor plus Equal® (NutraSweet®; aspartame).

Agent nos. 1, 2, and 3 were reported to be mildly flavored; about 1g/50 mL PFOB was necessary to produce acceptable masking. All seven tested samples were reported to mask the PFOB satisfactorily and were reported to be acceptable for patient use.

EXAMPLE 5

The four following flavoring agents were submitted for testing for preferred use concentration. The four agents include:

1) Carnation® Hot Cocoa mix, sugar free;
2) Sugar-free Kool-Aid®, cherry flavored;
3) Sugar-free Tang®; and
4) Sugar-free Crystal Light®, fruit punch flavor.

The concentrations recommended for use by the manufacturers are listed in Table 1 below. These concentrations offer only the barest guidelines; they do not necessarily apply when masking fluorocarbon, since none of the flavoring agent dissolves in the medium and only a small portion may contact the tongue and mouth mucous membranes. Also, as some of the flavoring agent floats on the surface, a larger portion of the flavoring agent may be ingested initially. The tested ranges given below are quantified using measuring spoons; it should be appreciated that the amounts may be varied according to individual taste requirements.

TABLE 1

| Flavoring Agent | Recommended Concentration | Equiv. Conc. per 50 mL | Grams ¼ tsp | Range Tested (tsp) |
|---|---|---|---|---|
| Carnation ® Hot Cocoa | 15.1 g/6 fl.oz | 4.26 g | 0.42 | ¼ to ½ |
| Kool-Aid ®, Cherry | 0.31 g/2 qt | 0.23 g | 0.66 | ⅛ to ¼ |
| Tang ® | 51 g/6 qt | 0.45 g | 0.78 | 1/16 to ¼ |
| Crystal Light ® Fruit Punch | 34 g/8 qt | 0.23 g | 0.79 | 1/16 to ¼ |

It should also be appreciated that a smaller proportion of flavoring agent may be adequate to provide masking when larger volumes than the 50 mL quantities tested herein are prepared.

Results

Teaspoonful-size quantities of 50 mL samples were tasted by test subjects. The following observations were made:

1) The taste of the Carnation® flavoring agent was very mild, and at least ½ teaspoon full would be required for full masking.
2) The taste of Kool-Aid® is slightly mild at ⅛ teaspoon; about ¼ teaspoonful is better.
3) The taste of Tang® was a bit too mild at 1/16 teaspoonful but masks much better at strengths of about ⅛ to ¼ teaspoonful.
4) Crystal Light® does not mask the "slick" mouth-feel at 1/16 teaspoonful; about ⅛ to ¼ teaspoonful is adequate to overcome "slickness".

EXAMPLE 6

Addition of liquid flavoring agents such as mint and citrus to PFOB were not found to be as satisfactory as the above-reported samples. For example, none of the flavoring agents were soluble or miscible with PFOB and essentially no flavor was imparted to the PFOB. All liquid flavoring agents tested simply floated on the surface and imparted an unpleasant taste or mouth-feel when ingested. For example, the addition of lemon flavor resulted in a turpentine-like flavor when ingested.

EXAMPLE 7

Since many flavor concentrates are not palatable when ingested and require proper dilution and/or combination with other ingredients such as sugars, thickeners, etc., some additional feasibility tests were performed. Dry, finely-divided flavoring agents (food and beverage products) were suspended in PFOB. Since the agents were not soluble in the PFOB, the flavor agent tended to be absorbed on the tongue and cheek mucous membranes. Immediately, when the appropriate flavor agent was used, a pleasant flavor as well as a good mouth-feel were achieved.

The following food and beverage products were used as flavoring agents when added to PFOB at the approximate concentration of about 0.5 grams per 50 mL:

1. Carnation® Hot Cocoa Mix
2. Ghirardelli® all-purpose ground chocolate and cocoa
3. Crystal Light® sugar-free lemonade mix
4. Raspberry Jell-o®, sugar-free Where necessary, lumps were ground up with mortar and pestle before addition. Powders could be suspended easily until ingested, although they eventually rose to the surface. The Carnation® and Ghirardelli® mixes had more of a granular, sugary mouth-feel which was not undesirable, according to test subjects. The lemonade and Jell-o® mixes contained finely powdered Nutrasweet® in place of sugar and remained in suspension much longer. It was reported that all of the above samples effectively mask the PFOB and are acceptable to the patient.

One subject reported that he could distinguish a slight PFOB slickness of the back of his tongue with the chocolate-flavored samples. Addition of a "bitter" note, such as caffeine in a coffee flavored sample was tested; a coffee-mocha combination proved to be acceptable. The Jell-o® and lemonade mix appeared to completely mask the slickness sensation.

Finally, optimization of the following aspects further improves the palatability of fluorocarbon contrast media: (1) flavor selections and use concentrations including recommendations for incorporating off-the-shelf items during clinical evaluation; (2) variations in powder size for improved suspension and mouth-feel; (3) added ingredients, such as filler ingredients, for improved mouth-feel, and/or for eliminating aftertaste; and (4) varying the temperature of the product when ingested.

EXAMPLE 8

In order to use the carbon dioxide generating compositions of the present invention in imaging the GI tract, the composition is orally administered to the patient. After carbon dioxide gas has been generated in the portion of the GI tract to be imaged, an image is formed using conventional X-ray, CAT scan, MRI, ultrasound, or other imaging technique in a manner that is well known.

EXAMPLE 9

Preparation of a composition according to the present invention is preferably accomplished by mixing together the individual components. For example, PFOB and hot cocoa mix were placed together in a container and mixed via shaking. Preferably, the particle size of the agent added to the fluorocarbon liquid is small enough to allow the agent to remain in suspension for about 2–3 minutes, which is typically long enough to allow administration of the admixture to a patient.

Compositions according to the present invention may be provided or sold in mixed or separate form. For example, the fluorocarbon and agent(s) may be provided in two separate, sealed containers; prior to administration to a patient, the contents of the container holding the agent may be poured into that holding the fluorocarbon. The mixture may then be agitated and administered to the patient.

Agents Tested

The various agents tested herein were selected largely because they were readily-available and in ready-to-use form. The list of agents tested is not to be considered as limiting the scope of the invention. There is no evidence indicating that the agents tested or contemplated by the present invention interfere with methods of imaging used, including MRI, CT and conventional radiography. As a further example of the variety of substances that may be effectively used with fluorocarbon liquids, the ingredients of the various agents used herein are listed below. They are not to be construed as limiting the scope of the invention; for example, sweeteners other than sugar or aspartame are certainly acceptable.

Crystal Light®
citric acid, potassium citrate, flavoring, aspartame, calcium phosphate or tricalcium phosphate, maltodextrin, lemon juice solids (for lemon-flavored variety), vitamin C, artificial color, BHA.

Unsweetened Kool-Aid®
citric acid, calcium phosphate, flavoring, vitamin C, artificial color.

Sugar-free Kool-Aid®
citric acid, maltodextrin, aspartame, calcium phosphate, artificial color, artificial flavor, vitamin C, salt.

Suisse Mocha-flavored Instant Coffee
non-dairy creamer (partially hydrogenated soybean oil, maltodextrin, sodium caseinate, dipotassium phosphate, mono-and diglycerides, lecithin), instant coffee, cocoa, maltodextrin, trisodium citrate, carrageenan, artificial flavor, aspartame.

Hershey's® or Ghirardelli® Cocoa
100% cocoa.

Sugar-free Carnation® Hot Cocoa
nonfat milk, cocoa, sweet dairy whey, salt, cellulose gum, aspartame, artificial vanilla flavor, disodium phosphate.

Artificial Creamer (e.g., ARA®)
corn syrup solids, partially hydrogenated vegetable oil (one or more of the following: soybean, canola, palm, palm seed, safflower, corn, sunflower, cottonseed), dipotassium phosphate, sodium caseinate, mono- and diglycerides, artificial color and flavor (some varieties also contain sodium silicoaluminate and/or lecithin).

Lipton® Sugar-free Iced Tea
maltodextrin, malic acid, instant tea, aspartame; some varieties also contain lemon flavoring.

Tang®
sugar, fructose, citric acid, calcium phosphate, potassium citrate, vitamin C, orange juice solids, calcium citrate, artificial color, flavoring, cellulose gum, xanthan gum, niacinamide, vitamin A palmitate, vitamin $B_6$, riboflavin (vit. $B_2$), folic acid; sugar-free varieties contain aspartame in place of the sugar and fructose.

Jell-o®
gelatin, adipic acid, maltodextrin, disodium phosphate, aspartame, fumaric acid, color, salt, flavor.

Equal® (NutraSweet®)
aspartame; Equal® tablets also contain lactose, leucine, maltodextrin, cellulose, and cellulose derivatives; Equals in powdered form also contains dextrose and maltodextrin.

The foregoing detailed description of the invention and the preferred embodiments, especially with respect to product compositions and processes, is to be considered illustrative of specific embodiments only. It is to be understood, however, that additional embodiments may be perceived by those skilled in the art. The embodiments described herein, together with those additional embodiments, are considered to be well within the scope of the present invention.

I claim:

1. A method for orally delivering a pharmacological or bioactive agent to a patient comprising administering an effective amount of a composition comprising a fluorocarbon liquid having said pharmacological or bioactive agent suspended therein.

2. The method of claim 1, wherein said agent is delivered in a time-release manner.

3. The method of claim 1, wherein said agent is encapsulated in a lipid or liposomal coating.

4. The method of claim 1, wherein the bioactive agent comprises an ulcer medication.

5. The method of claim 1 wherein said composition further comprises a palatability-enhancing agent.

6. The method of claim 5 wherein said palatability-enhancing agent is a flavoring agent.

7. The method of claim 1 wherein said composition firer comprises a non-toxic release-controlling substance.

* * * * *